United States Patent
Schwarz et al.

(10) Patent No.: US 6,200,791 B1
(45) Date of Patent: Mar. 13, 2001

(54) METHOD OF PURIFYING THROMBIN-LIKE PROTEASE ENZYMES OBTAINED FROM SNAKE VENOM

(75) Inventors: Margarete Schwarz, Deidesheim; Wolfgang Zahn, Altrip, both of (DE)

(73) Assignee: Knoll Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/125,374

(22) PCT Filed: Feb. 18, 1997

(86) PCT No.: PCT/EP97/00755

§ 371 Date: Aug. 17, 1998

§ 102(e) Date: Aug. 17, 1998

(87) PCT Pub. No.: WO97/32015

PCT Pub. Date: Sep. 4, 1997

(30) Foreign Application Priority Data

Feb. 26, 1996 (DE) .............................. 196 07 210

(51) Int. Cl.[7] .................................................. C12N 9/48
(52) U.S. Cl. ..................... 435/212; 435/814; 435/815
(58) Field of Search ................... 435/212, 814, 435/815

(56) References Cited

U.S. PATENT DOCUMENTS

| | | | |
|---|---|---|---|
| 3,743,722 | 7/1973 | Nolan | 424/542 |
| 3,879,369 | 4/1975 | Nolan | 530/413 |
| 4,027,012 | 5/1977 | Antonini | 424/542 |
| 4,137,127 | 1/1979 | Stocker | 435/219 |
| 5,712,117 * | 1/1998 | Sprecher | 435/69.2 |

FOREIGN PATENT DOCUMENTS

| | | |
|---|---|---|
| 24 28 955 | 3/1975 | (DE) . |
| 27 34 427 | 2/1978 | (DE) . |
| 1094301 | 12/1967 | (GB) . |
| 1177506 | 1/1970 | (GB) . |
| 1293793 | 10/1972 | (GB) . |

OTHER PUBLICATIONS

Merck Index, 11 Ed. 1989, p. 664.

Bonilla, "Defibrinating Enzyme from Timber Rattlesnake (Crotalus H. Horridus) Venom: A Potential Therapeutic for Defibrination I. Purification and Properties", Thromb. Res., 6(2), pp. 151–169, Feb. 1975.*

* cited by examiner

Primary Examiner—Jon P. Weber
(74) Attorney, Agent, or Firm—Keil & Weinkauf

(57) ABSTRACT

A process for purifying thrombin-like proteases from snake venoms is described, which consists in freeing the proteases from impurities in three chromatographic steps: a) affinity or anion exchange, b) adsorption onto a glass matrix at alkaline pH values, and c) size exclusion gel or glass matrix at acidic pH values.

6 Claims, No Drawings

METHOD OF PURIFYING THROMBIN-LIKE PROTEASE ENZYMES OBTAINED FROM SNAKE VENOM

This is a 371 of International application No. PCT/EP97/ 00755, filed Feb. 18, 1997.

The present invention relates to a process for purifying thrombin-like proteases from snake venoms.

Examples of such proteases are batroxobin, crotalase and, in particular, ancrod. The latter is an anticoagulant which is isolated from the venom of the snake Agkistrodon rhodostoma (Merck Index 1989, No. 664). A multiplicity of methods for its preparation from snake venom have already been described (GB Patent 1,094,301, GB Patent 1,177,506, GB Patent 1,293,793, U.S. Pat. No. 3,743,722, U.S. Pat. No. 3,879,369, German Offenlegungsschrift 2,428,955, German Offenlegungsschrift 2,734,427). These processes are essentially based on chromatographic steps and yield the ancrod in varying yield and purity.

The preparation of highly pure ancrod from snake venom has been unsuccessful until now. A mixture of enzymes with ancrod as the main component was always isolated which, depending on the preparation, was contaminated with more or less foreign proteins.

A way has now been found to prepare thrombin-like proteases from snake venoms in highly pure form.

The invention relates to a process for purifying thrombin-like proteases from snake venoms, which consists in a. subjecting a protease crude product to a prepurification by affinity chromatography or chromatography on a basic ion exchanger, b. subjecting the fraction containing the thrombin-like enzymes thus obtained to chromatography on a weak cation exchanger or separating it in the basic range by adsorption on glass and c. subjecting the main component from step b to gel chromatography or purifying this component in the acidic range by chromatography on glass, where, however, at least one of steps b and c comprises a separation by adsorption or chromatography on glass.

The invention furthermore relates to thrombin-like proteases from snake venoms in a purity of from 95 to 100%.

It is recommended for stage b to carry out the purification by adsorption on glass and stage c with the aid of gel chromatography.

In a particularly preferred embodiment of the invention, purification both in stage b and in stage c is carried out by adsorption or chromatography on glass.

Agmatine-, arginine- or heparin-Sepharose is particularly suitable for the prepurification by affinity chromatography.

Basic ion exchangers suitable for the prepurification are particularly DEAE-cellulose and DEAE-Sepharose.

Buffers which may be mentioned for ion exchange chromatography are, in particular, tris-phosphate and sodium phosphate buffers.

Ion exchange chromatography is carried out at a pH of 5–9, preferably of 6–8.5.

During the prepurification, approximately 70–80% of foreign proteins and other constituents are removed from the crude enzyme.

If the second step of the purification is carried out using a cation exchanger, those suitable are the following weakly acidic exchangers: CM-SEPHAROSE, pH 5–9, and AMBERLITE CG50, pH 5–9.

Chromatography on glass means that ancrod and related thrombin-like enzymes as well as strongly basic proteases are bound to the glass matrix at pHs of 7.5–9.0, preferably 8.0–8.5. About 60% of especially acidic foreign proteins are washed from the column in unbound form with the equilibration buffer (preferably tris-phosphate or sodium phosphate buffer). Ancrod is eluted from the glass fractionally in over 90% purity by increasing the ionic strength of the buffer to 0.3–1.0 M by addition of sodium chloride.

In the second purification step, the enzyme is concentrated to approximately 90%.

For gel chromatography as a purification step c, suitable gels, in particular, are: SEPHACRYL S-100HR, SUPERDEX, SEPHADEX, ULTROGEL and SUPEROSE.

If chromatography on glass is selected for this purification step c, in the acidic pH range from 4–6 basic foreign proteins are adsorbed on the glass surface from the ancrod solution, while ancrod can be eluted from the column directly in the equilibration buffer in far over 95% purity. The desired ionic strength of the buffer can be regulated by addition of a salt such as sodium chloride.

The novel process is very particularly suitable for the preparation of ancrod in pure form, which according to this purification process is obtained in a purity of clearly over 95%.

EXAMPLE 1 a. Prepurification 3 g of dried venom of the Malayan pit viper were dissolved in 50 ml of tris(hydroxymethyl)aminomethane (TRIS)-phosphate buffer pH 8.5, insoluble cell constituents of the venom were centrifuged off and the clear, yellow solution was applied to a chromatography column which had a diameter of 1.6 cm and was packed up to a height of 30 cm with DEAE-SEPHAROSE-FF (Pharmacia). The thrombin-like enzymes of the venom and the proteins having acidic character were bound to the matrix. Chromatography was carried out at a flow rate of 150–200 ml/h. By washing the column at room temperature with about 300 ml of equilibration buffer (10 mM TRIS-phosphate buffer pH 8.5) until the $A_{280\ nm}$ value of the eluate had fallen below 0.5 and further washing with 400 ml of 35 mM TRIS-phosphate buffer pH 6.0 until the $A_{280\ nm}$ value of the eluate was <0.4, about 70–80% of the foreign proteins (based on the optical density of the starting solution at 280 nm) were eluted. The main fraction containing ancrod was eluted in 85% yield in 150–200 ml of 150 mM TRIS-phosphate buffer pH 6.0.

b. Main purification

The eluate which contained the ancrod was concentrated to 20 ml by means of ultrafiltration on a membrane having a nominal separation limit of 10000 Daltons and rebuffered using a 100 mM TRIS-phosphate buffer pH 8.0. This solution was applied to a column which had a diameter of 1.6 cm and was packed up to a height of 15 cm with BIORAN-CPG glass beads (Schott, pore diameter: 25–35 nm, particle size: 30–60 μm). By washing the column at room temperature with 300 ml of the 100 mM TRIS-phosphate buffer pH 8.0 and at a flow rate of 250 ml per hour, about 60% of foreign proteins (based on the optical density of the material applied at 280 nm) were eluted from the column.

For elution, a 0.5 M sodium chloride solution which was buffered to a pH of 8.0 using 100 mM TRIS-phosphate was employed. The eluate was automatically collected in about 10 ml fractions. The thrombin-like enzymes were eluted in one peak with a subsequent tailing range. In order to obtain the main component (corresponds to ancrod) in a form which contained at most 5% of thrombin-like secondary components, in the transition from the main peak to the tailing range individual fractions were investigated by means of reverse-phase HPLC both for their specific fibrinogenase activity and for their composition. Only fractions which had a specific activity of greater than 1700 $U/OD_{280\ nm}$ and which contained less than 10% of secondary components in HPLC were combined with the main peak (about 80 ml). The main component was obtained from the BIORAN column in a purity of 96% and a yield of 72%.

c. Fine purification

The eluate containing the main component ancrod was concentrated to 2 ml by ultrafiltration on a YM 10 membrane (Amicon) and the concentrate obtained was applied to a column which had a diameter of 1.6 cm and was packed up to a height of 85 cm with SEPHACRYL S-100 HR. The column had been equilibrated beforehand using a buffer of 100 mM sodium chloride and 100 mM sodium phosphate which had a pH of 6.9. Residual proteases and TRIS were separated from ancrod by means of this gel chromatography. The yield in this step was about 90%.

EXAMPLE 2 a. Prepurification 2.1 g of dried venom of the Malayan pit viper were dissolved in 50 ml of 35 mM TRIS-phosphate buffer pH 8.5, insoluble cell constituents of the venom were centrifuged off and the clear, yellow solution was applied to a chromatography column which had a diameter of 1.6 cm, was packed up to a height of 30 cm with DEAE-SEPHAROSE-FF (Pharmacia) and was equilibrated with the buffer mentioned above. By washing the column at room temperature with 600 ml of equilibration buffer until the $A_{280\ nm}$ value of the eluate was <0.2, approximately 70% of the foreign proteins (based on the optical density of the starting solution at 280 nm) were eluted. The main fraction was eluted in 90–100% yield using 200–250 ml of 150 mM TRIS-phosphate buffer pH 6.0.

b. Main purification

The eluate was concentrated to 20 ml as in Example 1 and rebuffered using a 50 mM Na phosphate buffer pH 8.5. This solution was applied to the BIORAN-CPG glass column (diameter: 1.6 cm, height: 15 cm, pore diameter: 25–35 nm, particle size: 30–60 µm). By washing the column at room temperature with 300 ml of the 50 mM Na phosphate buffer pH 8.5 and at a flow rate of 250 ml per hour, about 60% of foreign proteins (based on the optical density of the material applied at 280 nm) were eluted from the column.

For elution of the thrombin-like enzymes, a 1 M sodium chloride solution which had been buffered to a pH of 8.0 using 50 mM Na-phosphate was employed. Using 150 ml of buffer, about 80% of the units of enzyme applied were eluted.

c. Fine purification

The eluate was concentrated to 20 ml as above and rebuffered using a 50 mM Na phosphate buffer which had a pH of 5.0. This solution was applied to a column which also had a diameter of 1.6 cm and was packed up to a height of 15 cm with BIORAN-CPG glass which, however, had a pore diameter of 90–110 nm and a particle size of 30–60 µm. At pH 5.0, only basic proteins and the secondary components were bound to the BIORAN glass, while the main component ancrod was eluted from the column using the equilibration buffer in a purity of approximately 100% and in about 80–90% yield (based on the units applied).

EXAMPLE 3 a, b. Pre- and main purification 2.1 g of dried venom of the Malayan pit viper were prefractionated on DEAE-SEPHAROSE analogously to Example 2, and the eluate was concentrated to 20 ml analogously to Example 1 and rebuffered using a 40 mM TRIS-phosphate buffer pH 6.2. This solution was applied to a chromatography column which had a diameter of 1.6 cm, [lacuna] packed up to a height of 20 cm with CM-SEPHAROSE-FF (Pharmacia) and was equilibrated with the abovementioned buffer. By washing the column at room temperature with 300 ml of the equilibration buffer and at a flow rate of 250 ml/h, about 60% of foreign proteins (based on the optical density of the material applied at 280 nm) were eluted from the column.

For elution of the thrombin-like enzymes, analogously to Example 2 a 1 M sodium chloride solution which was buffered to a pH of 8.0 using 50 mM Na phosphate was employed. Using 150 ml of buffer, about 80% of the units of thrombin-like enzymes applied were eluted.

c. Fine purification

The fine purification of ancrod was carried out analogously to Example 2 on BIORAN-CPG glass (pore diameter about 100 nm; particle size 30–60 µm) using a 50 mM phosphate buffer pH 5.0. Ancrod was eluted from the column in over 95% purity and in about 85% yield (based on the units applied).

We claim:

1. A method of purifying a thrombin-like protease from snake venom selected from the group consisting of ancrod and strongly basic proteases, which method comprises
    a) obtaining a solution comprising the protease;
    b) loading the protease solution onto an affinity chromatography matrix or an anion exchange resin;
    c) eluting the protease in an eluate solution from the affinity chromatography matrix or anion exchange resin;
    d) loading the eluate solution from step c) onto a matrix of glass beads; said glass beads having a pore diameter of from 25 to 35 nm and a particle size of from 30 to 60 µm; said eluate being applied to the matrix of glass beads in a basic solution at a pH value of from 7.5 to 9.0 whereby the glass beads adsorb the thrombin-like protease from snake venom;
    e) eluting the protease in an eluate solution from the matrix of glass beads;
    f) loading the eluate solution from step e) onto a size exclusion gel matrix or onto a matrix of glass beads; said glass beads having a pore diameter of from 25 to 35 nm and a particle size of from 30 to 60 µm; said eluate being applied to the matrix of glass beads in an acidic solution; and
    g) eluting and recovering the purified protease.

2. The method of claim 1, wherein the purification in step f) is carried out using a size exclusion gel matrix.

3. The method of claim 1, wherein the eluate solution is loaded onto a matrix of glass beads in step f).

4. The method of claim 1 in which the snake venom is from a snake of the genus Agkistrodon.

5. The method of claim 4 in which the snake venom is from *Agkistrodon rhodostoma*.

6. The method of claim 1 wherein the purified product is ancrod.

* * * * *